United States Patent [19]

Carr et al.

[11] Patent Number: 5,700,812
[45] Date of Patent: Dec. 23, 1997

[54] (+)-α-(2,3-DIMETHOXYPHENYL)-1-[2-(4-FLUOROPHENYL)ETHYL]-4-PIPERIDINEMETHANOL

[75] Inventors: Albert A. Carr; John M. Kane; David A. Hay, all of Cincinnati, Ohio

[73] Assignee: Merrell Pharmaceuticals Inc., Cincinnati, Ohio

[21] Appl. No.: 485,701

[22] Filed: Jun. 7, 1995

Related U.S. Application Data

[62] Division of Ser. No. 372,694, Jan. 13, 1995, Pat. No. 5,561,144, which is a continuation of Ser. No. 115,000, Aug. 31, 1993, abandoned, which is a continuation of Ser. No. 31,065, Mar. 12, 1993, abandoned, which is a continuation of Ser. No. 880,612, May 8, 1992, abandoned, which is a division of Ser. No. 736,194, Jul. 26, 1991, Pat. No. 5,134,149, which is a continuation-in-part of Ser. No. 531,954, Jun. 1, 1990, abandoned.

[51] Int. Cl.$^6$ ...................... A61K 31/445; C07D 211/22
[52] U.S. Cl. ............................................. 514/317; 546/241
[58] Field of Search ............................. 514/317; 546/241

[56] References Cited

U.S. PATENT DOCUMENTS

| | | | |
|---|---|---|---|
| 2,833,775 | 5/1958 | Sperber et al. | 546/241 |
| 3,655,676 | 4/1972 | Kaiser et al. | 546/241 |
| 4,623,728 | 11/1986 | Sarges | 546/236 |
| 4,762,842 | 8/1988 | Cohen et al. | 514/288 |
| 4,783,471 | 11/1988 | Carr | 514/317 |
| 4,877,798 | 10/1989 | Sorensen | 514/314 |
| 4,912,117 | 3/1990 | Carr | 514/317 |
| 5,021,428 | 6/1991 | Carr | 514/317 |
| 5,112,978 | 5/1992 | Molinari | 546/240 |
| 5,169,096 | 12/1992 | Carr | 514/317 |
| 5,618,824 | 4/1997 | Schmidt et al. | 514/317 |

FOREIGN PATENT DOCUMENTS

| | | |
|---|---|---|
| 0208235 | 1/1987 | European Pat. Off. . |
| 1316424 | 5/1970 | United Kingdom . |

OTHER PUBLICATIONS

*An electrophysiological investigation of the mechanism of action of the mechanism of action of the 5–ht2 antagonists ritanserin and mdl 28, 133a on amphetamine induced slowing of a 1q0 dopamine neurons*, abstract of presentation at International Congress on Schizophrenic Research present in Tuscon Arizona on Apr. 21–25, 1991.
*Psychopharmacology* (1989) 98:45–50: L. Ugedo wt al.
*Drugs of the Future* vol. 14, No. 5, 1989, pp. 489–490.
*Pharmacology and Toxicology Supplement* 1, 1990, 5–7, E. Christensson et al.
*Pharmacology and Toxicology Supplement* 1, 1990, 12–17, B. Gustaffson et al.
*Journal of Neurochemistry*, vol. 54, No. 3, 1990, 1062–1066, Nash et al.
*Psychopharmacology* (1989) vol. 99:S18–S27; H. Y. Meltzer.
*4–Aroylpiperidines and Related Carbinols as Potent and Selective Inhibitors of Serotonin 5–HT2 Receptors with Antipsychotic Potential*, Abstract of presentation at International Congress on Schizophrenic Research present in Tuscon Arizona on Apr. 21–25, 1991.

Primary Examiner—C. Warren Ivy
Assistant Examiner—D. Margaret M. Mach
Attorney, Agent, or Firm—Carolyn D. Moon

[57] ABSTRACT

The present invention is directed to a new $5HT_2$ antagonist, (+)-α-(2,3-dimethoxyphenyl)-1-[2-(4-fluorophenyl)ethyl]-4-piperidinemethanol, and its use in the treatment of a number of disease states.

1 Claim, No Drawings

(+)-α-(2,3-DIMETHOXYPHENYL)-1-[2-(4-FLUOROPHENYL)ETHYL]-4-PIPERIDINEMETHANOL

This is a division of application Ser. No. 08/372,694, filed Jan. 13, 1995 now U.S. Pat. No. 5,561,144, which is a continuation of application Ser. No. 08/115,000, filed Aug. 31, 1993, now abandoned, which is a continuation of application Ser. No. 08/031,065, filed Mar. 12, 1993, now abandoned, which is a continuation of application Ser. No. 07/880,612, filed May 8, 1992, now abandoned, which is a divisional of application Ser. No. 07/736,194, filed Jul. 26, 1991, issued as U.S. Pat. No. 5,134,149 on Jul. 28, 1992, which is a continuation-in-part of application Ser. No. 07/531,954, filed Jun. 1, 1990, now abandoned.

The present invention is directed to the compound (+)-α-(2,3-dimethoxyphenyl)-1-[2-(4-fluorophenyl)ethyl]-4-piperidinemethanol. Other aspects of this invention are directed to pharmaceutical compositions containing this compound and the medicinal use of this compound.

BACKGROUND OF THE INVENTION

European Application 0 208 235 disclosed a class of compounds which were described by the following formula:

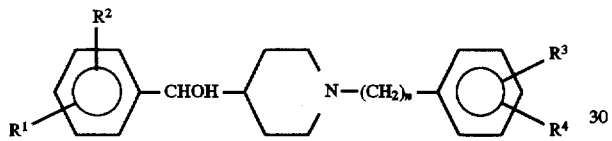

the optical isomers thereof, and the pharmaceutically acceptable salts thereof, wherein n is 2, 3, or 4, each of $R^1$, $R^2$, $R^3$, and $R^4$ is independently selected from hydrogen, halogen, trifluoromethyl, $C_{1-6}$ alkyl, $C_{1-6}$ alkoxy, hydroxy or amino. This application stated that the compounds were serotonin $5HT_2$ antagonists. Preferred compounds included those in which $R_1$ and $R_2$ were methoxy and in which $R_3$ and $R_4$ were hydrogen. The most preferred compound was that in which n was 2 and $R_{1-4}$ were hydrogen.

SUMMARY OF THE INVENTION

In accordance with the present invention, a new serotonin $5HT_2$ antagonist has been discovered which possesses superior in vivo potency. This compound is the (+)-isomer of α-(2,3-dimethoxyphenyl)-1-[2-(4-fluorophenyl)ethyl]-4-piperidinemethanol and the pharmaceutically acceptable salts thereof. It can be described by the following formula:

Formula I

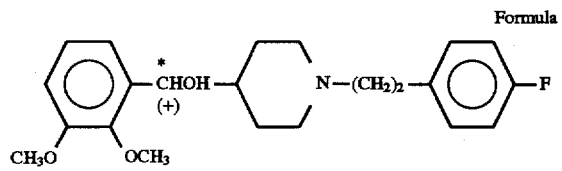

This compound and its method of preparation are generically described by European Application 0 208 235. This European Application does not specifically name (+)-α-(2,3-dimethoxyphenyl)-1-[2-(4-fluorophenyl)ethyl]-4-piperidinemethanol nor does it specifically exemplify its preparation.

Since (+)-α-(2,3-dimethoxyphenyl)-1-[2-(4-fluorophenyl)ethyl]-4-piperidinemethanol is a serotonin $5HT_2$ antagonist, it is effective in the treatment of a number of disease states. These disease states include anxiety, variant angina, anorexia nervosa, Raynaud's phenomenon, intermittent claudication, coronary or peripheral vasospasms, fibromyalgia, cardiac arrhythmias, thrombotic illness and in controlling the extrapyramidal symptoms associated with neuroleptic therapy.

DETAILED DESCRIPTION OF THE INVENTION

As used in this application:

a) the expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

b) any reference to (+)-α-(2,3-dimethoxyphenyl)-1-[2-(4-fluorophenyl)ethyl]-4-piperidinemethanol should be construed as encompassing the free base of this compound or an acid addition salt of this compound.

The (+)-isomer of α-(2,3-dimethoxyphenyl)-1-[2-(4-fluorophenyl)ethyl]-4-piperidinemethanol can be prepared by methods known in the art as was discussed in European Application 0 208 235. One suitable method is disclosed below in Reaction Scheme I:

REACTION SCHEME I

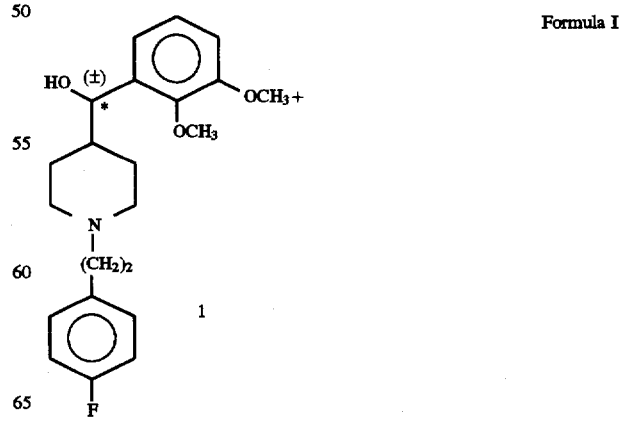

Formula I

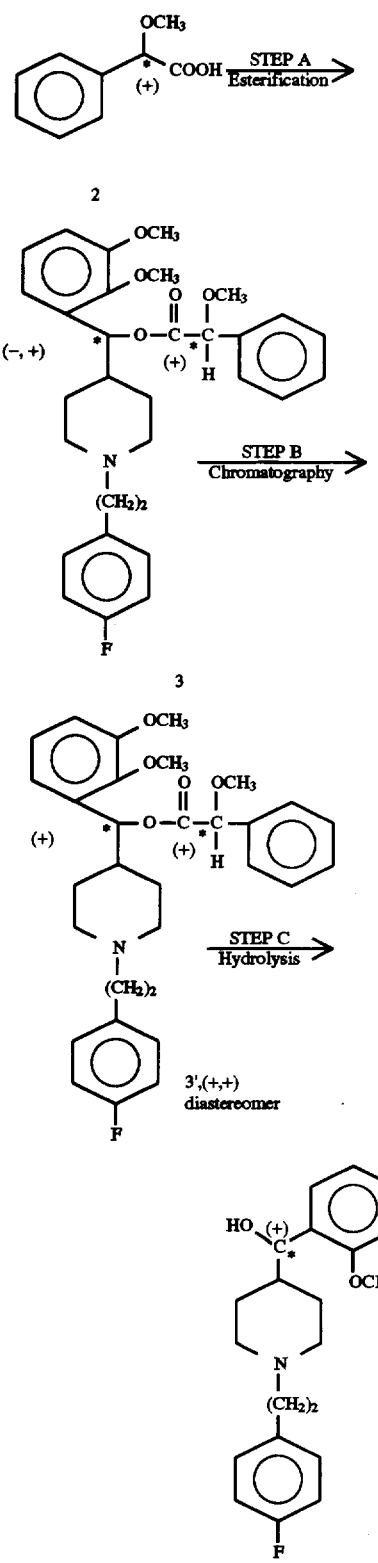

-continued
REACTION SCHEME I

In Step A of Reaction Scheme I, an esterification reaction is carried out between racemic α-(2,3-dimethoxyphenyl)-1-[2-(4-fluorophenyl)ethyl]-4-piperidinemethanol (structure 1) and the (+)-isomer of α-methoxyphenylacetic acid (structure 2). This esterification produces the diastereomeric mixture identifed as structure 3. These diastereomers are subjected to silica gel chromatography which separates the two diastereomers, thereby isolating the (+,+) diastereomer as is depicted in Step B. In Step C, the (+,+) diastereomer is hydrolysed which produces the (+)-isomer of α-(2,3-dimethoxyphenyl)-1-[2-(4-fluorophenyl)ethyl]-4-piperidinemethanol.

The esterification reaction can be carried out using techniques known in the art. Typically approximately equivalent amounts of racemic α-(2,3-dimethoxyphenyl)-1-[2-(4-fluorophenyl)ethyl]-4-piperidinemethanol and the (+)-isomer of α-methoxyphenylacetic acid are contacted in an organic solvent such as methylene chloride, THF, chloroform, toluene and heated to reflux for a period of time ranging from 5 to 24 hours. The esterification is typically carried out in the presence of an equivalent amount of dicyclohexylcarbodiimide and a catalytic amount of 4-dimethylaminopyridine. The resulting diastereomers can be isolated by filtration of the dicyclohexylurea and evaporation of the filtrate.

The diastereomers are then subjected to silica gel chromatograpy which separates the (+,+) and the (−,+) diastereomers. This chromatographic separation may be carried out as is known in the art. A 1:1 mixture of hexane and ethyl acetate is one suitable eluent.

The resulting (+,+) diastereomer is then subjected to a hydrolysis reaction which produces the (+)-isomer of α-(2,3-dimethoxyphenyl)-1-[2-(4-fluorophenyl)ethyl]-4-piperidinemethanol. The hydrolysis is carried out by contacting the diastereomer with an excess of a base such as potassium carbonate in an aqueous alcoholic solution. The hydrolysis is carried out at a temperature of about 15° C. to 30° C. for a period of time ranging from 2 to 24 hours. The resulting (+)-isomer of α-(2,3-dimethoxyphenyl)-1-[2-(4-fluorophenyl)ethyl]-4-piperidinemethanol may then be recovered by dilution with water and extraction with methylene chloride. It is then purifed by recrystallization from a solvent system such as cyclohexane/hexane or ethyl acetate/hexane.

Methods for producing the starting materials of Reaction Scheme I are known in the art. For example, U.S. Pat. No. 4,783,471 teaches how to prepare racemic α-(2,3-dimethoxyphenyl)-1-[2-(4-fluorophenyl)ethyl]-4-piperidinemethanol. This patent is hereby incorporated by reference. Examples No. 1 and 2 of this application also teach suitable methods. Alternatively, racemic α-(2,3-dimethoxyphenyl)-1-[2-(4-fluorophenyl)ethyl]-4-piperidinemethanol can be prepared in the following manner. Initially 4-hydroxypiperidine is subjected to an N-alkylation reaction with p-fluorophenylethyl bromide which produces 4-hydroxy-1-[2-(4-fluorophenyl)ethyl]-piperidine. This compound is brominated with $Ph_3P.Br_2$ which produces 4-bromo-1-[2-(4-fluorophenyl)ethyl] piperidine. This compound is contacted with Mg thereby forming a Grignard Reagent which is then reacted with 2,3-dimethoxybenzaldehyde which produces the desired product (±)-α-(2,3-dimethoxyphenyl)-1-[2-(4-fluorophenyl)ethyl]-4-piperidinemethanol. The (+)-isomer of α-methoxyphenylacetic acid is known in the art.

As noted above, it has been discovered that the (+)-isomer of α-(2,3-dimethoxyphenyl)-1-[2-(4-fluorophenyl)ethyl]-4-piperidinemethanol possesses superior in vivo potency when compared with the other compounds encompassed by the European Application described above, EP 208 235. The ability of this compound to antagonize the $5HT_2$ receptor in vivo can be demonstrated via the (5-MeO-DMT) head twitch test as described by Friedman et al., in *Commun. Psychopharmacol.*, Vol. 3, pages 89–92, (1979). The administration of 5-methoxy-N,N-dimethyltryptamine 5-MeO-DMT to mice typically produces a characteristic head twitch in the mice. In this test, the mice are administered 5-MeO-DMT and a test compound. An absence of head twitches in the mice is considered to be predictive of the ability of the test compound to antagonize the $5HT_2$ receptor in vivo.

Table I reports the $ED_{50}$ of (+)-α-(2,3-dimethoxyphenyl)-1-[2-(4-fluorophenyl)ethyl]-4-piperidinemethanol (Invention). For comparative purposes, it also reports the $ED_{50}$ of α-phenyl-1-(2-phenylethyl)-4-piperidinemethanol (Compound B) as its racemate and as its (+)-isomer and α-(2,3-dimethoxyphenyl)-1-(2-phenylethyl)-4-piperidinemethanol (Compound C). These compounds were identified as being the most preferred species of the EPO 208 235 application. The European applicaton does not specify which isomer of these compounds is preferred.

TABLE III

| Compound | $ED_{50}$ FOR ABOLITION OF HEAD TWITCH (mg/kg, ip) |
|---|---|
| Invention | 0.03 |
| Compound B | |
| a) racemic | 3.28 |
| b) (+)-isomer | 0.87 |
| Compound C | |
| a) racemic | 2.04 |

The dosage range at which (+)-α-(2,3-dimethoxyphenyl)-1-[2-(4-fluorophenyl)ethyl]-4-piperidinemethanol exhibits its ability to block the effects of serotonin at the $5HT_2$ receptor can vary depending upon the particular disease or condition being treated and its severity, the patient, other underlying disease states the patient is suffering from, and other medications that may be concurrently administered to the patient. Generally though, this compound will exhibit its serotonin $5HT_2$ antagonist properties at a dosage range of from about 0.001 mg/kg of patient body weight/day to about 100.0 mg/kg of patient body weight/day. The compound is typically administered from 1–4 times daily. Alternatively, it can be administered by continuous infusion. The compounds can be administered orally or parenterally to achieve these effects.

Since the compound is a serotonin $5HT_2$ antagonist, it is useful in the treatment of a variety of disease states and conditions. It is useful in the treatment of anxiety, variant angina, anorexia nervosa, Raynaud's phenomenon, intermittent claudication and coronary or peripheral vasospasms. These conditions and diseases can be relieved by administering to a patient in need thereof of, (+)-α-(2,3-dimethoxyphenyl)-1-[2-(4-fluorophenyl)ethyl]-4-piperidinemethanol, in an amount sufficient to treat the disease or condition (i.e. an anxiolytic amount, anti-anginal amount, anti-anorexic amount, etc.). This quantity will be within the dosage range at which the compound exhibits its serotonin $5HT_2$ antagonistic properties.

(+)-α-(2,3-dimethoxyphenyl)-1-[2-(4-fluorophenyl)ethyl]-4-piperidinemethanol is also useful in the treatment of fibromyalgia. As used in this application, fibromyalgia refers to a chronic disease state wherein the patient suffers from numerous symptoms such as, for example, widespread generalized musculoskeletal pains, aching, fatigue, morning stiffness and a sleep disturbance which can be characterized as an inadequacy of stage 4 sleep. Administration of this compound, in an anti-fibromyalgia amount relieves or alleviates the symptoms the patient is experiencing. An anti-fibromyalgia amount will be within the dosage range described above wherein this compound exhibits its serotonin $5HT_2$ antagonist effect.

This compound can also be used to treat the extrapyramidal symptoms that often accompany the administration of neuroleptic agents such as haloperidol, chlorpromazine, etc. These extrapyramidal side effects (EPS) can manifest themselves in a variety of ways. Some patients experience a parkinsonian-like syndrome, wherein they experience muscular rigidity and tremors. Others experience akathisia, which can be characterized as a compelling need for the patient to be in constant movement. A few patients experience acute dystonic reactions, such as facial grimacing and torticollis. The administration of this compound to a patient in need thereof, in an anti-EPS amount, will relieve or alleviate the symptoms that the patient is experiencing. The amount of compound which produces this anti-EPS effect is an amount within the dosage range at which this compound exhibits its serotonin $5HT_2$ antagonistic effect.

As used in this application:

a) the terms "anxiety, variant angina, anorexia nervosa, Raynaud's phenomenon, and coronary vasospasms" are used in the manner defined in the 27th Edition of Dorland's Illustrated Medical Dictionary;

b) the term "patient" refers to a warm-blooded animal, such as for example rats, mice, dogs, cats, guinea pigs, and primates such as humans, and;

c) the term "treat" refers to either relieving or alleviating the patient's disease or condition.

(+)-α-(2,3-dimethoxyphenyl)-1-[2-(4-fluorophenyl)ethyl]-4-piperidinemethanol also possess antiarrhythmic properties. It increases the duration of the action potential of myocardial tissue producing an increase in the refractory period of that tissue. Thus, under the classification system of Vaughan Williams, this compound exhibits a Class III antiarrhythmic activity.

Since the compound is a Class III antiarrhythmic, it will be useful for treating a variety of arrhythmic conditions of the heart. Representative examples of arrhythmic conditions which are amendable to treatment with the compounds of the present invention include supra ventricular arrhythmias such as atrial tachycardia, atrial flutter, atrial fibrillation, and life threatening ventricular arrhythmias such as ventricular tachycardia, or ventricular fibrillation. This compound will also prevent recurrent episodes of the arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, and the presence of other underlying disease states. However as a general guideline, if the compound is being administered orally, then it is preferably administered within a dosage range of from about 1.0 to about 400 mg/kg of patient body weight/day. Likewise, if the compound is being administered parenterally then it is preferably administered within a dosage range of from about 0.1 to about 100 mg/kg of patient body weight/day. The patient's response to the compound can be monitored via an EKG or any other technique conventionally used in the art.

As used in this application:

a) the term arrhythmia refers to any variation from the normal rhythm of the heart beat, and;

b) the term antiarrhythmic refers to a compound capable of either preventing or alleviating an arrhythmia.

(+)-α-(2,3-dimethoxyphenyl)-1-[2-(4-fluorophenyl) ethyl]-4-piperidinemethanol is also useful in the treatment of thrombotic illness. A thrombus is an aggregation of blood factors, primarily platelets and fibrin with entrapment of other formed elements of the blood. Thrombi can also consist of primarily platelet aggregates. Thrombi are typically formed in order to prevent excessive bleeding from injured blood vessels. Thrombi are typically formed in the following manner.

The vascular endothelium serves as a barrier between the blood-borne platelets which continually circulate throughout the body and the proaggregatory subendothelial components, which are primarily collagen. In addition to serving as a physical barrier, the cell membranes of the endothelial lining contain negatively charged components which serve to create an electrostatic repulsion between the platelets and the lining of the vessels. Trauma to the blood vessel will disrupt this endothelial lining and allow the platelets to come in contact with the underlying collagen and fibronectin. This causes the platelets to adhere to the sub-endothelial surface. This initial adherence causes the release, from these platelets, of a number of chemicals such as adenosine diphosphate, serotonin, and thromboxane $A_2$, all of which have a proaggregatory effect upon the initial platelet aggregate or plug and stimulate other circulating platelets to adhere to this newly formed plug. The additional adherence of these platelets stimulate the further release of these proaggregatory chemicals, which causes further growth of the platelet plug. Thus a self-perpetuating cycle is initiated which promotes the growth of the plug.

In addition to adhering to the injured vascular wall and forming aggregates, activated platelets accelerate the generation of thrombin which acts to convert the plasma protein, fibrinogen, into fibrin, thereby stabilizing the thrombus and promoting its growth. Prior to the conversion of fibrinogen into fibrin, a sequence of enzymatic conversions take place on the platelet surface which ultimately leads to the formation of fibrin. Both the negatively charged phospholipids on the platelet surface and calcium are essential for the maximal activation of Factor X. Once Factor X is activated, prothrombin is converted to thrombin which cleaves fibrinogen into fibrin and activates Factor XIII. This Factor catalyzes the crosslinking reaction of fibrin which stabilizes the platelet mass. In addition, thrombin is a powerful platelet activator and will act to perpetuate the process.

Thus once the platelets come in contact with the subendothelial surface, a reaction is initiated in which a number of positive feedback control systems act to produce a thrombus which blocks off the affected vasculature. The entire process (ie. platelet aggregation, fibrin generation, and polymerization) is referred to as hemostasis and is important in the prevention of excessive bleeding from the wound.

Although the formation of thrombi is desirable in a bleeding vessel, it is pathological in an intact vessel. Thrombi occur in intact vessels due to minor alterations in the endothelial cell surface or injuries that result in the disruption of the endothelial linings. Even relatively minor alterations can allow the platelets to come in contact with collagen and initiate the process described above. These minor alterations occur from a variety of causes. These causes include stasis, (ie. decreased movement of blood in the cardiac chambers or blood vessels) which induces damage due to lack of oxygen and reduces the shear forces that ordinarily discourage platelet interaction. Another cause is the damage which the process of atherosclersis inflicts upon the endothelial linings. Endothelial linings are known to be disrupted at the site of atherosclerotic lesion.

Thus, a significant amount of research has been focused on finding drugs which will prevent the platelets from undergoing aggregation due to these minor alterations which are commonly found on the endothelial linings. Part of the research has been directed at exploring what effect could be achieved by administering an antagonist of serotonin, one of the proaggregatory substances which is released when the platelets initially begin to aggregate. Although serotonin is a relatively weak proaggregatory factor, it has been discovered that serotonin has a synergistic effect upon the primary proaggregatory clotting factor, ADP. Thus serotonin amplifies the proaggregatory effect of ADP.

Ketanserin is a serotonin antagonist. It reacts at the $5HT_2$ receptor. Bush et al. reported this compound was extremely effective in preventing thrombus formation in canine models which have been designed to screen for this activity. *Drug Development Research Vol.* 7, pages 319–340 (1986).

It has been discovered that (+)-α-(2,3-dimethoxyphenyl) -1-[2-(4-fluorophenyl)ethyl]-4-piperidinemethanol is also effective in the prevention of acute thrombosis, especially those of the coronary arteries. This compound decreases the rate at which platelets aggregate as the result of minor alterations in the endothelial lining of the vasculature and therefore prevent the formation of acute pathological thrombi.

Since the compound is effective as an antithrombotic agent, it can be utilized in a variety of clinical settings in which a patient is at risk of developing pathological acute thrombi. As noted above, it should be administered on a prophylactic basis to prevent the occurrence of an acute thrombotic episode, not to lyse thrombi which have already occurred.

For example, patients who have undergone thrombolysis with agents such as tissue plasminogen activator are at a high risk of suffering subsequent acute coronary artery thrombosis. This compound can be administered to these patients to prevent them from suffering additional acute coronary artery thrombotic episodes and any ensuing myocardial infarction.

It can also be used to decrease the time for re-establishing patent blood flow with thrombolysis, since it prevents acute thrombotic episodes. Acute thrombotic episodes routinely occur in patients undergoing thrombolysis and prolong the time required to re-establish patent blood flow. Patients who have undergone either a coronary bypass procedure or angioplasty are also typically at a greater risk of suffering thrombosis and thus can benefit from treatment as well. Other patients who will benefit from therapy include patients with saphenous vein bypass grafts, preventative therapy for acute occlusion after coronary angioplasty, secondary prevention of stroke recurrence, thrombosis of arteriovenous cannula in patients on hemodialysis and to prevent the occurrence of stroke and coronary thrombosis in patients with atrial fibrillation.

The compound can also be administered to patients to prevent the occurrence of transient ischemic attacks (TIA). These attacks result from the formation of platelet emboli in severely atherosclerotic arteries, usually one of the carotid arteries, and these attacks are the forerunners of cerebral thrombus, i.e., stroke.

Thus the compound can be used to prevent the occurrence of pathological acute thrombotic or embolic episodes. In order to achieve this result it is necessary that the compound be administered to the patient in an antithrombotic quantity. The dosage range at which this compound exhibits this antithrombotic effect can vary depending upon the severity of the thrombotic episode, the patient, other underlying disease states the patient is suffering from, and other medications that may be concurrently administered to the patient. Generally though, this compound will exhibit an antithrombotic effect at a dosage range of from about 0.001 mg/kg of patient body weight/day to about 100 mg/kg of patient body weight/day. The administration schedule will also vary widely, but will typically be from 1 to 4 times daily. This compound can be administered by a variety of routes. It is effective if administered orally or parenterally.

If desired, the compound can be administered in combination with other antiaggretory substances, such as, for example, aspirin (300–1200mg/day), dipyridamole (300–400 mg/day), ticlopidine (50–500mg/day), warfarin (25–300 mg/day), hirudin (0.1–100 mg/kg/day), or MDL 28,050. The compound can also be administered in combination with a thromboxane synthetase inhibitor, such as, for example, ozagrel, dazmegrel, SQ 29,548, or SQ 30,741. These thromboxane synthetase inhibitors are typically administered at a dosage range of from 0.5–50 mg/kg/day. The compound and the thromboxane synthetase inhibitors can be compounded into a single dosage form and administered as combination product. Methods for producing such dosage forms are well known in the art.

As used in this application, the term "antithrombotic" should be construed as referring to the ability to either prevent or decrease the formation of acute pathological thrombi or emboli. It should not be construed as referring to the ability to dissolve a thrombus that has already formed. For the purpose of this application, the difference between a thrombus and an embolus, is that an embolus can be be an entire thrombus or a portion of a thrombus, that produces occlusion by moving to the site of occlusion from other parts of the circulation. It is not produced at the site of occlusion as is a thrombus.

One of the significant problems associated with drug abuse is the high rate of relapse among patients in drug rehabilitation programs. A large percentage of patients in these programs ultimately resume their pattern of drug abuse after discharge from a rehabilitation center. It has been discovered that the compounds of Formula I can be utilized in patients recovering from drug abuse to decrease the likelihood of their relapse and readdiction to drugs. Current research indicates that these patients return to their addicted states in an attempt to return to the positive affective state produced by drug abuse (J. Stewart, et al, *Psychological Reviews* 91:251–268, 1984, and M. A. Bozarth and R. A. Wise, NIDA Res. Monogr. 67:190–6, 1986).

Recent research also indicates certain drugs of abuse produce this positive affective state by causing the release of dopamine in the nucleus accumbens region of the brain (meso limbic area) (Carboni, E., Acquas, E. Frau, R. & Di Chiara, G. (1989) *European Journal of Pharmacology*, 164, 515–519; Di Chiara, G. & Imperato, A. *Journal of Pharmacology and Experimental Therapeutics*, 244, 1067–1080; H. C. Fibiger et al, *Annals of the New York Academy of Sciences* 537:206–215, 1988 and C. J. Schmidt, et al, J. *Pharmacol Exp. Ther.* 256:230–235, 1991). Since nucleus accumbens dopamine release is the incentive for continued drug abuse, compounds blocking the release of dopamine and/or its physiological effects in this area of the brain would prevent the patient from receiving gratification via drug abuse. Compounds interfering with dopamine in this area of the brain could be utilized to remove the motivation to resume one's drug habits.

Schmidt et al has shown that serotonin $5HT_2$ antagonists inhibit the release of dopamine in the CNS. Meert et al has shown that the $5HT_2$ antagonist, ritanserin, abolished the preference for both alcohol and cocaine in a rodent model of drug abuse (T. F. Meert, et al, *European Journal of Pharmacology*, 183, 1924).

The compounds of Formula I are serotonin $5HT_2$ antagonists. They can be utilized in the treatment of drug abuse to remove the gratification obtained from drug abuse and decrease the likelihood of readdiction. These compounds can be utilized to prevent patients from becoming readdicted to alcohol, nicotine, opiates and psychostimulants such as cocaine, amphetamine, methamphetamine, dextroamphetamine, etc.

The compounds effectiveness in treating drug abuse can be demonstrated in in-vivo animal models known in the art. One such model is the rodent self-stimulation model as described in R. A. Frank, et al, (1987) *Behavioral Neuroscience*, 101, 546–559. In this model, rats are implanted with bipolar stimulating electrodes in the ventral tegremental area of the brain. The rats are trained to stimulate themselves and a control current is established. This group is then given cocaine, for example, and a second level of stimulation is established. Drugs of abuse, such as cocaine, typically lower the level of current that is required for self-stimulation. The test compound is then administered in the presence of cocaine or another drug of abuse. If the compound is preventing the effects of dopamine in the mesolimbic area, then the level of current required for stimulation returns toward the control level. Other models include C. Kornetsky, et al. *Testing and Evaluation of Drugs of Abuse*, New York, Wiley-Liss, 1990 and J. R. Stellar, et al, *The Neuropharmacological Basis of Reward*, Oxford U.K., Clarendon Press, 1989.

In order to exhibit this anti-drug abuse potential, the compounds need to be administered in a quantity sufficient to inhibit the release of dopamine in the mesolimbic area of the brain. The dosage range at which these compounds exhibit this effect can vary widely depending upon the particular drug of abuse, the severity of the patient's addiction, the patient, the route of administration, and the presence of other underlying disease states within the patient, etc. Typically the compounds exhibit their effects at a dosage range of from about 0.001 mg/kg/day to about 100 mg/kg/day. Repetitive daily administration may be desirable and will vary according to the conditions outlined above. Typically, the compounds will be administered from 1–4 times daily.

As used herein "treating drug abuse" refers to the compounds ability to negate the gratification which the individual receives from abusing drugs, thereby removing the motivation to resume previous drug habits or establish new ones.

Since the compounds of Formula I inhibit the release of dopamine in the CNS, they will be effective in the treatment of psychotic illnesses such as schizophrenia, mania, etc. The dosage range at which these compounds exhibit this antipsychotic effect can vary widely depending upon the particular disease being treated, the severity of the patient's disease, the patient, the route of administration, and the presence of other underlying disease states within the patient, etc. Typically the compound exhibits its antipsychotic effects at a dosage range of from about 0.001 mg/kg/day to about 100 mg/kg/day. Repetitive daily administration may be desirable and will vary according to the conditions outlined above. Typically, the compounds will be administered from 1–4 times daily.

As used in this application:

a) the term "psychosis" refers to a condition where the patient, e.g., a human, experiences a major mental disorder of organic and/or emotional origin characterized by derangement of the personality and loss of contact with reality, often with delusions, hallucinations or illusions. Representative examples of psychotic illnesses which can be treated with the compounds of the present invention include schizophrenia, and mania.

As noted above, the compounds are useful in the treatment of variant angina. Patients suffering from variant angina experience coronary vasospasms which produce the chest pains typically associated with angina. These vasospams typically occur while the patient is at rest. Patients suffering from stable angina experience these pains in response to the increased myocardial oxygen consumption associated with exercise, emotion, etc. Patients with stable angina typically have extensive coronary atherosclerosis.

Serotonin produces a biphasic response in normal coronary vessels (ie. those without significant atherosclerotic damage). Low concentrations of serotonin produce coronary dilation, whereas higher concentrations produce constriction. Patients suffering from variant angina have an abnormal response to serotonin and experience constriction at doses much lower than normal individuals. Therefore serotonin $5HT_2$ antagonists benefit these patients by blocking this abnormal response to serotonin.

McFadden et al recently reported that patients with stable angina do not show a biphasic response to serotonin. Intracoronay infusion of serotonin induced constriction of the coronary vessels in these patients at all concentrations tested. The patients also experienced anginal attacks during these infusions. New England Journal of Medicine 1991; 324:648–654. Golino et al also reported similar findings. New England Journal of Medicine 1991; 324:641–648. Golino et al reported that ketanserin, a $5HT_2$ antagonist, blocked coronary vessel constriction in patients with stable angina. McFadden et al and Golino et al stated that their findings suggest that serotonin, released after the intracoronary activation of platelets, contributes to or causes myocardial ischemia in patients with coronary artery disease.

Since the compounds of Formula I are serotonin $5HT_2$ antagonists, they are useful in the treatment of both variant angina and stable angina (anigna pectoris). The compounds of Formula I can be used on a prophylactic basis to prevent the occurrence of angina or they can be administered to a patient experiencing an anginal attack to terminate that attack. The amount of compound which produces this antianginal effect is an amount within the dosage range at which the compounds exhibit their serotonin $5HT_2$ antagonistic effects.

The compound can be formulated into pharmaceutical dosage forms using techniques well known in the art. For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compound can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compound or its salts may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compound may be admixed with any inert carrier and utilized in laboratory assays in order to determine the concentration of the compounds within the urine, serum, etc. of the patient as is known in the art.

The following Examples are being presented to further illustrate the invention. However, they should not be construed as limiting the invention in any manner.

EXAMPLE 1

Example 1, Steps A–D, demonstrates the preparation of the starting material (±)-α-(2,3-dimethoxyphenyl)-1-[2-(4-fluorophenyl)ethyl]-4-piperidinemethanol, structure 1.

A) 1-[2-(4-Fluorophenyl)ethyl]-4-piperidinecarboxamide

A solution of isonipecotamide (10.9 g, 85.0 mmol), 2-(4-fluorophenyl)ethyl bromide (15.7 g, 77.3 mmol), and $K_2CO_3$ (2.3 g, 167 mmol) was prepared in DMF (280 mL) and stirred under argon at 90°–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2× with water, dried ($MgSO_4$), filtered, and evaporated to a oily solid. The solid was recrystallized from EtOAc to afford 1-[2-(4-fluorophenyl)ethyl]-4-piperidinecarboxamide as a white powder, m.p. 177°–178° C. (decomp.). Anal. Calcd for $C_{14}H_{19}FN_2O$: C, 67.18; H, 7.65; N, 11.19. Found: C, 67.25; H, 7.67; N, 11.13.

B) 4-Cyano-1-[2-(4-fluorophenyl)ethyl]piperidine

To stirred phosphorus oxychloride (25 mL, 41.12 g, 268 mmol) and sodium chloride (5.1 g, 87.3 mmol) was added 1-[2-(4-fluorophenyl)ethyl]-4-piperidinecarboxamide (8.9 g, 35.6 mmol) portionwise. After complete addition, the solution was refluxed for 2 hours. The cooled solution was poured into dilute $NH_4OH$ to destroy the $POCl_3$. The aqueous solution was cooled to 0° C., then extracted 2× with $CH_2Cl_2$. The combined organic layers were dried ($MgSO_4$), filtered, and evaporated to afford 8.1 g of an oily solid. The solid was distilled, (b.p. 150° C., 0.1 mm Hg), to afford a clear, colorless oil that solidified. This material was crystallized from hexane to afford 4-cyano-1-[2-(4-fluorophenyl) ethyl]piperidine as white needles, m.p. 47°–48° C. Anal. Calcd for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl) ethyl]piperidine (1.00 g, 4.3 mmol) in THF (20 mL) under argon at 0° C. was added DIBAL-H (4.6 mL of a 1.0M solution in THF, 4.6 mmol) via syringe. After stirring overnight at room temperature, 10% aqueous HCl (25 mL) was added and the solution was stirred for 3 hours. The entire mixture was then poured into 10% aqueous NaOH (50 mL), then extractd 2× with ether. The combined organic layers were washed with brine, dried ($MgSO_4$), filtered, and evaporated to afford a pale yellow oil. The oil was chromatographed on silica gel, eluting with EtOAc. The appropriate fractions were combined and evaporated to afford an oil. This oil was distilled (b.p. 166° C., 0.05 mm Hg) to afford 1-[2-(4-fluorophenyl)ethyl]-4-piperidinecarboxaldehyde, obtained as a colorless oil. Anal.

Calcd for $C_{14}H_{18}FNO$: C, 71.46; H, 7.71; N, 5.95. Found: C, 71.08, H, 7.81; N, 5.86.

D) (±)-α-(2,3-Dimethoxyphenyl)-1-[2-(4-fluorophenyl) ethyl]-4-piperidinemethanol To a stirred solution of veratrole (0.93 g, 6.7 mmol) in THF (20 mL) under argon at 0° C. was added n-BuLi (2.7 mL of a 2.5M solution in hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an addition funnel. The cooling bath was removed and the solution was allowed to stir for 2 hours. Water was added, the layers separated, and the aqueous layer was extracted with EtOAc. The combined organic layers were washed with brine, dried (MgSO$_4$), filtered, and chromatographed on silica gel, eluting with acetone. The appropriate fractions were combined and evaporated to afford a white solid. The solid was recrystallized from hexane to afford racemic α-(2,3-dimethoxyphenyl)-1-[2-(4-fluorophenyl)ethyl]-4-piperidinemethanol as shiny white needles, m.p. 126°–127° C. Anal. Calcd for $C_{22}H_{28}FNO_3$: C, 70.75; H, 7.56; N, 3.75. Found: C, 70.87; H, 7.65; N, 3.68.

EXAMPLE 2

Example 2, Steps A–F, demonstrate an alternative manner of preparing (±)-α-(2,3-dimethoxyphenyl)-1-[2-(4-fluorophenyl)ethyl]-4-piperidinemethanol, structure 1.

A) 1-(1,1-Dimethylethyl)-1,4-piperidinedicarboxylic acid

To isonipecotic acid (107.5 g, 832 mmol) stirred in 1N NaOH (40 g NaOH in 900 mL H$_2$O) and tert-butanol (1800 mL) was added di-tert-butyl dicarbonate (200 g, 916 mmol) in portions. After stirring overnight, the solution was concentrated and the resulting water layer was acidified with aqueous HCl. This acidic aqueous layer was extracted 3× with ether. The combined organic layers were washed with water, brine, dried (MgSO$_4$), filtered, and evaporated to a white solid, which was recrystallized from EtOAc/hexane (300 mL/200 mL) to afford 1-(1,1-dimethylethyl)-1,4-piperidinedicarboxylic acid as white needles, m.p. 147°–149° C.

B) 4-(N-Methoxy-N-methylcarboxamido)-1-piperidinecarboxylic acid 1,1-dimethylethyl ester To a stirred solution of 1-(1,1-dimethylethyl)-1,4-piperidinedicarboxylic acid (50.0 g, 218 mmol) in anhydrous CH$_2$Cl$_2$ (500 mL) under N$_2$ in a 2 L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl, twice with saturated NaHCO$_3$, once with brine, dried (MgSO$_4$), filtered, and evaporated to an oil. Distillation afforded 4-(N-methoxy-N-methylcarboxamido)-1-piperidinecarboxylic acid 1,1-dimethylethyl ester as a clear oil, b.p. 120°–140° C., 0.8 mm.

C) 4-(2,3-Dimethoxybenzoyl)-1-piperidinecarboxylic acid 1,1-dimethylethyl ester n-Butyl lithium (14.5 mL of a 2.5M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous NH$_4$Cl was added and the mixture was allowed to stir overnight. The layers were separated and the aqueous layer was extracted with ether. The combined organic layers were washed with brine, dried (MgSO$_4$), filtered, and evaporated to afford an amber oil. The oil was chromatographed on silica gel, eluting with 20% EtOAc in hexane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil. (b.p. 225°–250° C., 0.05 mm). Anal. Calcd for $C_{19}H_{27}NO_5$: C, 65.31; H, 7.79; N, 4.01. Found: C, 65.04; H, 7.92; N, 4.11.

D) 4-(2,3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd for $C_{14}H_{19}NO_3 \cdot CF_3CO_2H$: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried (MgSO$_4$), filtered, and evaporated to afford 4-(2,3-dimethoxyphenyl)-4-piperidinylmethanone as an oil.

E) (2,3-Dimethoxyphenyl)[1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4-fluorophenyl)ethyl bromide (6.52 g, 32.1 mmol) was prepared in DMF (90 mL), treated with K$_2$CO$_3$ (7.0 g, 50.7 mmol), then stirred and heated at 80° C. under argon overnight. The cooled solution was poured into a partition of 2/1 EtOAc/toluene and water. The layers were separated and the aqueous layer was extracted with 2/1 EtOAc/toluene. The combined organic layers were washed 2× with water, 1× with brine, dried (MgSO$_4$), filtered, and evaporated to afford 11.0 g of an oil. The oil was chromatographed on silica gel, eluting with EtOAc. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225°–227° C. (decomp). Anal Calcd for $C_{22}H_{26}FNO_3 \cdot HCl$: C, 64.78; H, 6.67; N, 3.43. Found: C, 64.44; H, 6.73; N, 3.41.

F) (±)-α-(2,3-Dimethoxyphenyl)-1-[2-(4-fluorophenyl) ethyl]-4-piperidinemethanol To a stirred solution of (2,3-dimethoxyphenyl)[1-[2-(4-fluorophenyl)ethyl]-4-piperidinyl]methanone (6.0 g, 16.2 mmol) in MeOH (100 mL) at 0° C. was added NaBH$_4$ (1240 mg, 32.8 mmol) in two portions, over a one hour period. After stirring overnight, the solution was concentrated to a solid. The solid was partitioned between water and ether. The layers were separated and the aqueous layer was extracted with ether. The combined organic layers were washed with brine, dried (MgSO$_4$), filtered, and evaporated to a solid. The solid was chromatographed on silica gel, eluting with acetone. The appropriate fractions were combined and evaporated to afford a white solid. The solid was recrystallized from cyclohexane to afford (±)-α-(2,3-dimethoxyphenyl)-1-[2-(4-fluorophenyl)-ethyl]-4-piperidinemethanol as white needles, m.p. 126°–127° C. Anal. Calcd for $C_{22}H_{28}FNO_3$: C, 70.75; H, 7.56; N, 3.75. Found: C, 70.86; H, 7.72; N, 3.93.

EXAMPLE 3

This example demonstrates the preparation of the compound of Formula I.

Preparation of (+)-α-(2,3-Dimethoxyphenyl)-1-[2-(4-fluorophenyl)ethyl]-4-piperidinemethanol A) Preparation of diastereomers.

A solution of 3.90 g (10.4 mmol) of (±)-α-(2,3-dimethoxyphenyl)-1-[2-(4-fluorophenyl)ethyl]-4-piperidinemethanol, 1.74 g (10.4 mmol) of S-(+)-α-methoxyphenylacetic acid, 2.15 g (10.4 mmol) of 1,3-dicyclohexylcarbodiimide and 0.1 g of 4-dimethylaminopyridine in chloroform (75 ml) was refluxed for 17 hours, allowed to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were rechromatographed to give additional material. Those fractions with Rf=0.2 were combined to give a single diastereomeric ester, (+,+)-(2,3-dimethoxyphenyl)[1-[2-(4-fluorophenyl)ethyl]-4-piperidinyl]methyl-α-methoxybenzeneacetate.

B) Preparation of (+)-α-(2,3-Dimethoxyphenyl)-1-[2-(4-fluorophenyl)ethyl]-4-piperidinemethanol To a stirred solution of 0.97 g (1.9 mmol) of the above mentioned diastereomeric ester, Rf=0.2, in 25 ml of methanol was added 0.5 g (3.6 mmol) of potassium carbonate and 5.0 ml of water. After stirring 17 hours at room temperature the reaction mixture was diluted with water and extracted twice with methylene chloride. The combined extracts were washed with water, brine and dried over $MgSO_4$. After filtering, the filtrate was concentrated to an oil and crystallized from 40 ml of cyclohexane/hexane (1:1) to give (+)-α-(2,3-dimethoxyphenyl)-1-[2-(4-fluorophenyl)ethyl]-4-piperidinemethanol, m.p. 112°–113° C., $[\alpha]_D^{20}$=+13.9°.

What is claimed is:

1. A method for the treatment of coronary vasospasms comprising administering to a patient in need thereof, an anti-spasmodic amount of (+)-α-(2,3-dimethoxyphenyl)-1-[2-(4-fluorophenyl)ethyl]-4-piperidinemethanol, or a pharmaceutically acceptable salt thereof.

* * * * *